United States Patent [19]

Warring

[11] Patent Number: 4,808,168

[45] Date of Patent: Feb. 28, 1989

[54] PNEUMONEEDLE

[75] Inventor: Jessica A. Warring, Millbrae, Calif.

[73] Assignee: Endotherapeutics, Menlo Park, Calif.

[21] Appl. No.: 865,072

[22] Filed: May 19, 1986

Related U.S. Application Data

[63] Continuation-in-part of Ser. No. 859,228, May 5, 1986, abandoned, which is a continuation of Ser. No. 764,358, Aug. 9, 1985, abandoned.

[51] Int. Cl.⁴ .............................................. A61M 5/00
[52] U.S. Cl. .................................... 604/158; 604/170; 604/248
[58] Field of Search ...................... 604/170, 164–169, 604/272, 158, 248, 256

[56] References Cited

U.S. PATENT DOCUMENTS

| | | | |
|---|---|---|---|
| 1,527,291 | 2/1925 | Zorraquin | 604/158 |
| 2,623,521 | 12/1952 | Shaw | 604/170 |
| 3,713,447 | 1/1973 | Adair | 604/169 |
| 3,774,604 | 11/1973 | Danielsson | 604/169 |
| 4,403,617 | 9/1983 | Tretinyak | 604/170 X |
| 4,555,773 | 8/1985 | Yoon | 604/169 X |

*Primary Examiner*—Stephen C. Pellegrino
*Attorney, Agent, or Firm*—Ciotti & Murashige, Irell & Manella

[57] ABSTRACT

A single-use Veress-type pneumoneedle that has a flanged handle and a fixed valve subassembly that permit the pneumoneedle to be gripped like a syringe when it is being inserted. The stylet body is either a solid rod or a hollow tube. Insufflating gas is carried into the abdominal cavity through the lumen of the needle when the stylet is a solid rod or through the stylet lumen when the stylet is a hollow tube.

8 Claims, 2 Drawing Sheets

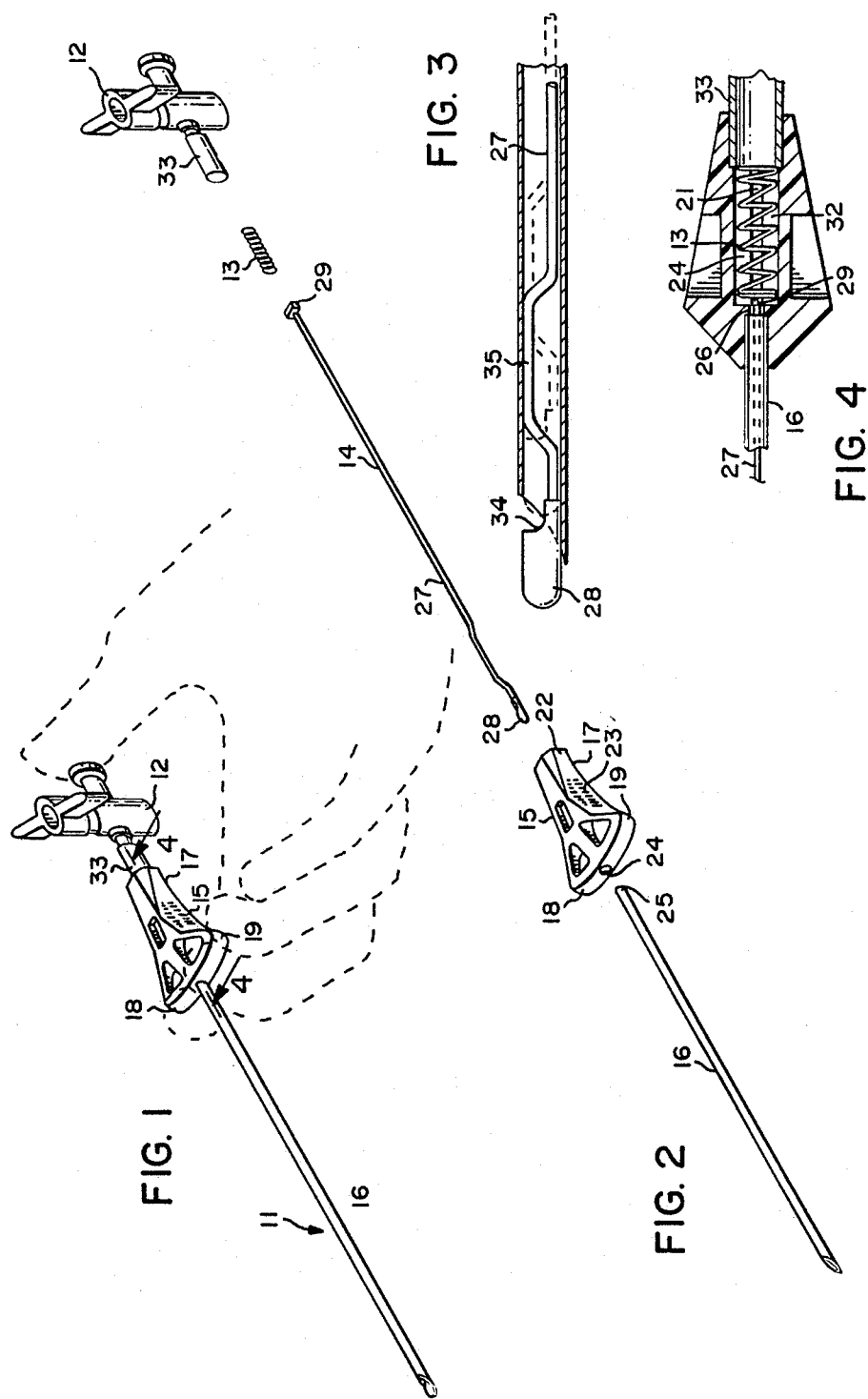

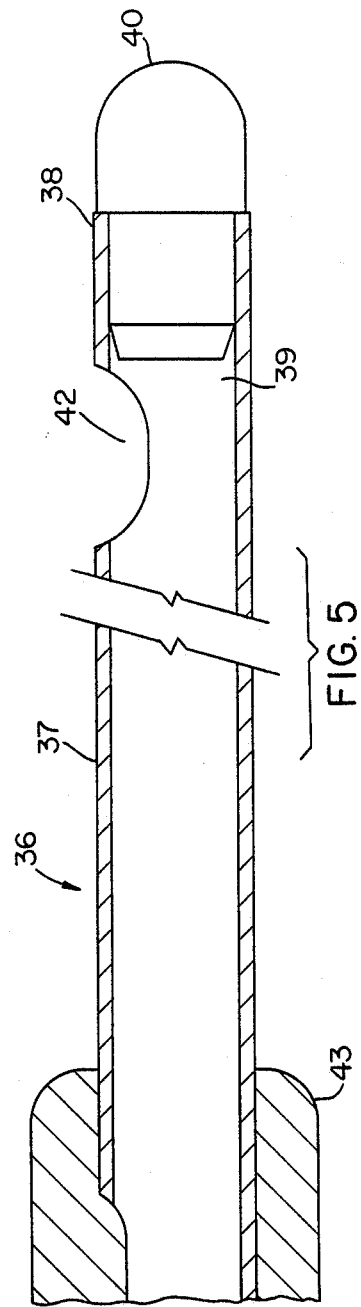
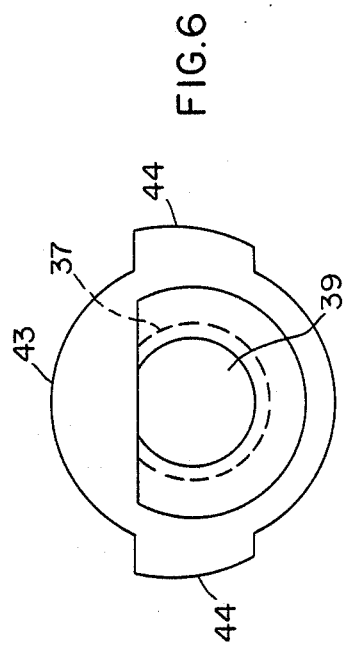

PNEUMONEEDLE

CROSS-REFERENCE TO RELATED APPLICATIONS

This application is a continuation-in-part of copending U.S. patent application Ser. No. 859,228 now abandoned, filed May 5, 1986, which in turn is a file wrapper continuation of U.S. patent application Ser. No. 764,338, filed Aug. 9, 1985, now abandoned.

DESCRIPTION

1. Technical Field

This invention is in the field of surgical instruments. More particularly, it relates to a single-use Veress-type pneumoneedle that is particularly useful in abdominal endoscopy.

2. Background Art

Pneumoneedles were introduced by Veress in the late 1930s to insufflate the abdominal cavity to facilitate endoscopic examination. The Veress-type pneumoneedle has a spring-loaded blunt stylet in a larger diameter hollow needle. Once the pneumoneedle penetrates the abdominal wall and enters the cavity the resistance against the end of the pneumoneedle ceases and the spring pushes the blunt end of the stylet forward so that it extends beyond the sharp tip of the needle. This helps to prevent puncture or laceration of the intraabdominal structures by the sharp tip of the needle.

Prior Veress-type pneumoneedles have used a hollow stylet with a side hole to carry the insufflating gas into the cavity and a longitudinally slidable valve assembly connected to the stylet. Both the stylet and valve assembly are pushed rearward by resistance on the needle end and are biased forward by the spring when the resistance is removed. Because of this design, the body of the needle must be grasped forwardly of the movable valve subassembly like a dart. Current Veress-type pneumoneedles are usually made from precision machined stainless steel parts and are expensive. They are, accordingly, intended for multiple reuse and must be cleaned and sterilized between uses and sharpened regularly.

DISCLOSURE OF THE INVENTION

The invention is directed to a Veress-type pneumoneedle that has a simpler design and is easier to hold and manipulate than prior pneumoneedles. Because of its simple design, it may be made for single-use, thereby obviating the need for repeated cleaning and sterilization, and resharpening.

The Veress-type pneumoneedle of the invention comprises in combination:

(a) an elongated handle having a longitudinal bore and flanges at one of its ends to permit the handle to be grasped like a syringe;

(b) a hollow needle for penetrating a body cavity and providing a conduit through which fluid may be passed to or from the cavity, the needle being fixed in the end of the bore at the flanged end of the handle;

(c) a nonremovable stylet having a solid rodlike body that extends through the lumen of the needle and into the bore and has a blunt tip at its forward end and a base member at its other end within the bore;

(d) a spring housed within the bore with one of its ends seated against the stylet base member for biasing the stylet forwarding so that the blunt tip extends outwardly of the needle tip in the absence of resistance; and (e) a valve connected fixedly to the bore at the end opposite the flanges for regulating fluid flow through the needle.

BRIEF DESCRIPTION OF THE DRAWINGS

In the drawings, which are not to scale:

FIG. 1 is a perspective view of an embodiment of the invention pneumoneedle being held like a syringe;

FIG. 2 is an exploded, perspective view of the pneumoneedle of FIG. 1;

FIG. 3 is an enlarged, schematic, cross-sectional view of the leading end of the pneumoneedle of FIG. 1;

FIG. 4 is an enlarged cross-sectional view of a portion of the pneumoneedle of FIG. 1 taken along line 4—4;

FIG. 5 is an enlarged cross-sectional view of an alternative, preferred embodiment of the pneumoneedle stylet; and FIG. 6 is an end view of the stylet of FIG. 5 looking at the base or hub.

MODES FOR CARRYING OUT THE INVENTION

FIGS. 1 and 2 depict an embodiment, generally designated 11, of the invention. The leading or forward end of the pneumoneedle is on the left-hand side of FIGS. 1 and 2. Its elements are best seen in FIG. 2 and are: a two-way stopcock type valve 12, a coil spring 13, a stylet 14, a handle 15, and a hollow needle 16.

Handle 15 functions as the main body of the device with the other elements being housed or attached to it. The handle is generally T-shaped with a generally flat sided stem 17 and a pair of integral flanges 18, 19. As shown in phantom in FIG. 1, this configuration allows the pneumoneedle to be gripped like a syringe with the thumb against the rear of the stopcock and the first and middle fingers against the front edges of the flanges on either side of the needle 16. The opposed sidewalls 22 of the handle stem are equipped with ridges 23 in the event that it is necessary or desirable to hold the pneumoneedle between the thumb and first finger by the stem in conventional dartlike fashion. As seen in FIG. 4, the handle has a central longitudinal bore 24 in which the other elements of the device fit or are housed.

End 25 of the hollow needle is fixed in the leading end of bore 24. As shown in FIG. 4, the bore has an internal shoulder at 26 that acts as a stop. The stylet 14 has a solid rod-shaped body 27 that is slidably received axially through the lumen of the needle. The stylet body carries a blunt tip 28 at its leading end and a radially extending base member 29 on its other end. Bore 24 has an enlarged diameter section 32 to accommodate the stylet base. The base extends from side-to-side across section 32 with its ends received in a pair of diametrically opposed axial slots or grooves 21 in the sidewall of section 32. This arrangement prevents the stylet from rotating. Nozzle 33 of the stopcock is fixed in the rearward end of bore 24. The coil spring 13 is housed within section 32 of the bore with one end seated against the stylet base and the other end seated against the leading end of the stopcock nozzle.

In the normal extended position of the stylet (seen in FIG. 3 in solid lines and in FIG. 4) the spring biases the stylet forward so that the stylet base rests across the opening to the forward section of the bore with its edges seated against the shoulder formed by the transition between the smaller diameter forward bore section and the larger diameter rearward section 32. The base is configured so that is does not block the opening entirely when it is so positioned. Such configuration permits fluid to pass unrestricted through the bore. In the retracted position (seen in FIG. 3 in phantom), force against the blunt end 28 forces the stylet rearwardly so that the base is spaced from the opening to the forward section of the bore.

In the pneumoneedle depicted in FIGS. 1-4, the insufflating gas flows through the lumen of the needle rather than through the stylet. In order to facilitate the flow of gas from the end of the needle, the stylet tip has a cutaway section 34 (FIG. 3). Also, the stylet body 27 has a step 35 in it that prevents radial (transverse to the longitudinal axis) displacement of the stylet tip and possible jamming of the tip in the needle opening.

An alternative and preferred stylet, generally designated 36, is shown in FIGS. 5 and 6. Stylet 36 has an axially elongated, hollow, tubelike body 37. The diameter of body 37 is slightly smaller than the diameter of the lumen of the needle. The leading end 38 of the lumen 39 of the stylet is plugged with a blunt tip 40. A slot 42 is located in the wall of the body immediately rearwardly of the tip and opens into the lumen 39. The rear end of the lumen opens into the bore of the handle of the pneumoneedle. The rear end of the stylet body carries a generally cylindrical base or hub member 43 that functions in the same manner as the base 29 of the stylet of FIG. 1-4. The base 43 has a pair of flange members 44 that function as the ends of base 29.

Stylet 36 operates similarly to stylet 14 except that the fluid (insufflating gas) is carried through the lumen of the stylet and into the body cavity via slot 42 rather than directly via the lumen of the needle. In operation, when the stylet is retracted, the slot 42 is generally masked by the needle. When the resistance is removed from the end of ths stylet, the stylet is advanced by the spring to fully expose the slot 42, thereby allowing fluid to flow freely through the lumen of the stylet into the body cavity. Because of the snug fit of the stylet 36 in the needle lumen, there is no possibility of radial displacement of the stylet and jamming of the tip in the needle opening.

The needle and stylet body may be made of rigid, biocompatible materials such as stainless steel. The handle and stopcock may be made of molded plastic for economy. The section of the handle that houses the coil spring is preferably transparent so that the position of the stylet base can be seen to determine whether the stylet is extended or retracted.

When the pneumoneedle is being inserted through the abdominal wall, the stopcock is in the closed position to prevent the internal abdominal pressure from equilibrating with ambient pressure after penetration. The pneumoneedle is inserted into the cavity in the conventional manner except that it may be held like a syringe if desired. During penetration, resistance from the abdominal wall causes the stylet to retract and expose the sharp tip of the needle. Once the wall has been penetrated, there is no resistance and the stylet automatically advances under the influence of the coil spring to blunt the end of the device. Insufflating apparatus (not shown) is then connected to the stopcock inlet. The inlet is conveniently adapted to receive a luer lock connector for this purpose.

In addition to being used to inflate body cavities with gas, the pneumoneedle may be used to withdraw fluid from body cavities. In such use, the needle is inserted into the desired location and suction is applied to the valve inlet.

Modifications of the above-described embodiments that are obvious to those of skill in the fields of medical instruments, mechanical design, or related fields in view of the foregoing disclosure are intended to be within the scope of the invention.

I claim:
1. A Veress-type pneumoneedle comprising:
   (a) an elongated handle having a longitudinal bore and flanges at one of its ends to permit the handle to be grasped like a syringe;
   (b) a hollow needle for penetrating a body cavity and providing a conduit through which fluid may be passed to or from the cavity, the needle being fit in the end of the bore at the flanged end of the handle;
   (c) a nonremovable stylet having an elongated body that extends through the lumen of the needle and into the bore and has a blunt tip at its forward end and a base member at its other end within the handle bore;
   (d) a spring housed within the bore with one of its ends seated against the stylet base member for biasing the stylet forwardly so that the blunt tip extends outwardly of the needle tip in the absence of resistance; and
   (e) a valve connected fixedly to the bore at the end opposite the flanges for regulating fluid flow through the needle.

2. The pneumoneedle of claim 1 wherein the stylet body is hollow and provides said conduit, the lumen of the stylet is closed at its forward end by said tip and opens at its other end into the bore, and the stylet body has a slot proximate its forward end that opens into the lumen of the stylet.

3. The pneumoneedle of claim 1 wherein the valve is a stopcock having a nozzle that is fixed in the end of the bore opposite the flanged end of the handle, and the other end of the spring is seated on the end of the nozzle.

4. A Veress-type pneumoneedle comprising:
   (a) an elongated handle having a longitudinal bore and flanges at one of its ends to permit the handle to be grasped like a syringe;
   (b) a hollow needle for penetrating a body cavity and providing a conduit through which fluid may be passed to or from the cavity, the needle being fit in the end of the bore at the flanged end of the handle;
   (c) a nonremovable stylet hanving an elongated body that extends through the lumen of the needle and into the bore and has a blunt tip at its forward end and a base member at its other end within the handle bore said stylet body being a solid rod having a substantially smaller diameter than the needle lumen so that fluid may pass through the needle lumen when the stylet body is within the lumen;
   (d) a spring housed within the bore with one of its ends seated against the stylet base member for biasing the stylet forwardly so that the blunt tip extends outwardly of the needle tip in the absence of resistance; and
   (e) a valve connected fixedly to the bore at the end opposite the flanges for regulating fluid flow through the needle.

5. The pneumoneedle of claim 4 wherein the stylet body has a radially displaced step segment in it to prevent radial displacement of the stylet body in the lumen of the needle.

6. The pneumoneedle of claim 4 wherein the stylet body has a radially displaced step segment in it to prevent radial displacement of the stylet body in the lumen of the needle, and the bore has a pair of opposed axial slots in its sidewall into which the ends of the base member are received to prevent the stylet from rotating.

7. A Veress-type pneumoneedle comprising:
(a) an elongated handle having a longitudinal bore and flanges at one of its ends to permit the handle to be grasped like a syringe;
(b) a hollow needle for penetrating a body cavity and providing a conduit through which fluid may be passed to or from the cavity, the needle being fit in the end of the bore at the flanged end of the handle;
(c) a nonremovable stylet having an elongated body that extends through the lumen of the needle and into the bore and has a blunt tip at its forward end and a base member at its other end within the handle bore that is received in a pair of opposed axial slots in the sidewall of the bore that do not open radially through the handle whereby the stylet is prevented from rotating within the lumen;
(d) a spring housed within the bore with one of its ends seated against the stylet base member for biasing the stylet forwardly so that the blunt tip extends outwardly of the needle tip in the absence of resistance; and
(e) a valve connected fixedly to the bore at the end opposite the flanges for regulating fluid flow through the needle.

8. A Veress-type pneumoneedle comprising:
(a) an elongated handle having a longitudinal bore and flanges at one of its ends to permit the handle to be grasped like a syringe;
(b) a hollow needle for penetrating a body cavity, the needle being fit in the end of the bore at the flanged end of the handle;
(c) a nonremovable stylet having an elongated hollow body that extends through the lumen of the needle and into the bore and has a blunt tip at its forward end, a base member at its other end within the handle bore and a slot proximate its forward end that opens into the lumen of the stylet said base member having a pair of opposed flange members and the bore having a pair of opposed axial slots in its sidewall that do not open radially through the handle and into which the flange members are received to prevent the stylet from rotating within the needle lumen and wherein the lumen of the stylet is closed at its forward end by said tip and opens at its other end into the bore and provides a conduit through which fluid may be passed to or from the cavity;
(d) a spring housed within the bore with one of its ends seated against the stylet base member for biasing the stylet forwardly so that the blunt tip extends outwardly of the needle tip in the absence of resistance; and
(e) a valve connected fixedly to the bore at the end opposite the flanges for regulating fluid flow through the needle.

* * * * *